United States Patent [19]

Baust

[11] Patent Number: 5,124,078

[45] Date of Patent: Jun. 23, 1992

[54] EXTRA MILD SHOWER GEL OR HAIR SHAMPOO FORMULATION

[75] Inventor: Heinrich Baust, Plankstadt, Fed. Rep. of Germany

[73] Assignee: Joh. A. Benckiser GmbH, Ludwigshafen, Fed. Rep. of Germany

[21] Appl. No.: 571,144

[22] Filed: Aug. 23, 1990

[30] Foreign Application Priority Data

Sep. 14, 1989 [DE] Fed. Rep. of Germany ....... 3930725

[51] Int. Cl.[5] .................... C11D 1/90; C11D 1/06; C11D 1/12; A61K 7/50
[52] U.S. Cl. ..................................... 252/546; 252/550; 252/174.21; 252/547; 252/135; 252/174.23; 252/174.11; 252/DIG. 5; 252/DIG. 7; 252/DIG. 13
[58] Field of Search ................ 252/DIG. 13, DIG. 5, 252/8.8, 174.17, 174.22, 174.23, 546, 547, 550, DIG. 7; 424/70

[56] References Cited

U.S. PATENT DOCUMENTS

| | | | |
|---|---|---|---|
| 3,950,417 | 4/1976 | Verdicchio | 424/70 |
| 3,990,991 | 11/1976 | Gerstein | 252/542 |
| 4,080,310 | 4/1978 | Ng | 252/DIG. 7 |
| 4,265,782 | 5/1981 | Armstrong | 252/DIG. 13 |
| 4,422,855 | 12/1983 | Sawyer | 252/315.1 |
| 4,439,417 | 5/1984 | Matsunaga | 424/70 |
| 4,664,835 | 5/1987 | Grollier | 252/174.22 |
| 4,719,104 | 1/1988 | Patel | 424/70 |
| 4,844,891 | 7/1989 | Rosen | 424/70 |
| 4,885,107 | 12/1989 | Wetzel | 252/DIG. 13 |

FOREIGN PATENT DOCUMENTS

| | | |
|---|---|---|
| 0099987 | 2/1984 | European Pat. Off. . |
| 2847439 | 5/1980 | Fed. Rep. of Germany . |
| 3414090 | 10/1984 | Fed. Rep. of Germany . |
| 3910652 | 4/1990 | Fed. Rep. of Germany . |

OTHER PUBLICATIONS

STN Registry File—completed Nov. 14, 1990 at 18:42:32.
Hawkley's Condensed Chemical Dictionary 1987 p. 176 col. 1.

*Primary Examiner*—Paul Lieberman
*Assistant Examiner*—Erin M. Higgins
*Attorney, Agent, or Firm*—Foley & Lardner

[57] ABSTRACT

The present invention provides a shower gel or hair shampoo which includes a neutralized tenside combination of alkyl polyglycol ether carboxylate, alkyl sulphate and fatty acid amidopropylbetaine, as well as conventional adjuvant and carrier materials, wherein the average degree of ethoxylation of the alkyl polyglycol ether carboxylate is from 2 to 5 ethoxy groups.

18 Claims, No Drawings

EXTRA MILD SHOWER GEL OR HAIR SHAMPOO FORMULATION

BACKGROUND OF THE INVENTION

The present invention relates to a new, extra-mild shower gel and hair shampoo formulation having a low tenside concentration.

The production amount for shower baths and hair shampoos in the cosmetics industry in Germany is, at the present moment, about 110,000 tons per year. The amount of tenside in commercially available products ranges from 15 to 25 weight %. Consequently, about 20,000 tons of tensides per year enter the waste water system where they are broken down more or less quickly and completely. A reduction of the wash-active substances is an object worth striving for not only from an economic but also from an ecological point of view.

It is known that in ether sulphate-containing formulations, due to their strong foam formation, a drastic reduction of the wash-active substances from, for example, 20% to 10% and below is possible and the accompanying decrease of viscosity can be compensated for by the addition of electrolytes, for example, sodium chloride and sodium sulphate, which load the waste water. The resulting salt loading exceeds the tenside concentration which, on the one hand, clearly increases the risk of eye burning and, on the other hand, also clearly increases the shower gel or hair shampoo's instability, i.e., the salting-out effect. Independent of this drawback, ether sulphate-containing tensides include pharmacologically hazardous dioxane in trace amounts.

Known ether sulphate-free tenside systems cannot be thickened sufficiently in the case of low tenside concentrations of 10% and below by the addition of electrolytes. Therefore, these systems require additional thickeners which have a negative effect on the properties of the products (foam structure, conditioning and the like) and increase the costs. Accordingly, it generally can be said that ether sulphate-free tenside combinations do not possess a sufficient thickening ability despite the salt loading and have weak foaming properties.

SUMMARY OF THE INVENTION

It is therefore an object of the present invention to provide an ether sulphate-free, mild and good foaming tenside combination for care of the skin and hair having, in the case of tenside concentrations of below 10%, a high viscosity but with a minimum of electrolyte salts and no additional thickeners.

In accomplishing the foregoing object there is provided according to the present invention, a shower gel or hair shampoo comprising a neutralized tenside combination of alkyl polyglycol ether carboxylate, alkyl sulphate and fatty acid amidopropylbetaine, as well as conventional adjuvant and carrier materials, wherein the average degree of ethoxylation of the alkyl polyglycol ether carboxylate is from about 2 to 5, ethoxy groups.

Further objects, features and advantages of the present invention will become apparent from the detailed description of preferred embodiments that follows.

DETAILED DESCRIPTION OF THE PREFERRED EMBODIMENTS

As described in Federal Republic of Germany Patent Application No.P 39 10 652.7, a tenside combination of lauryl polyglycol ether carboxylate, lauryl sulphate and lauric acid amidopropylbetaine with 2-10% sodium chloride gives a readily compatible shower gel. The lauryl glycol ether carboxylate has a degree of ethoxylation of 8 to 10 ethoxy groups. In order to produce a sufficient foaming behavior, a total tenside concentration of 15 to 20% was necessary. For adjustment of the viscosity, 4.5% of sodium chloride was added thereto.

Surprisingly, by utilizing a more aggressive alkyl ether carboxylic acid having a low degree of ethoxylation (2-5 ethoxy groups) in the compositions according to the present invention, skin irritations no longer occur and the compositions display such a strong foam formation capability that total tenside concentrations of below 10% are possible.

An alkyl polyglycol ether carboxylate in the context of the present invention is a compound of the general formula:

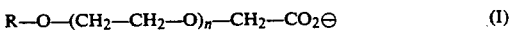

$$R-O-(CH_2-CH_2-O)_n-CH_2-CO_2^{\ominus} \qquad (I)$$

wherein R is an alkyl radical containing up to 20 carbon atoms, preferably 10 to 16 carbon atoms and especially 12 to 14 carbon atoms and n is an integer or fractional number of from 2 to 5, preferably about 2.5. The carboxylates are preferably neutralized with sodium, potassium or ammonium ions and especially with tris-(hydroxymethyl)aminomethane ("Tris").

In the case of the polycondensation of the glycol units, mixtures result which, for use as tensides, are not separated or only roughly separated. Therefore, the number n is to be understood to be the average value of the compounds obtained.

The alkyl sulphate used in the present invention may be monoalkyl sulphuric acid esters derived from fatty alcohols which are well-known for use as a tenside. Because of its especially good foaming behavior, lauryl sulphate is preferred.

The fatty acid amidopropylbetaine used in the present invention are those which are well-known as tensides. As fatty acids, those with 8 to 20 carbon atoms are typical. Because of the optimum foaming behavior and the combined effect with the two other components in the sense of a good thickening, without a sparingly soluble precipitate resulting, lauryl amidopropylbetaine is preferred.

The shower gel and hair shampoo compositions according to the present invention preferably include fatty acid amidopropylbetaine, lauryl sulphate and alkyl polyglycol ether carboxylate in a ratio ranging from about 1:1.5:1.8 to 1:3.2:4.3.

A further advantage of the mixtures according to the present invention resides in the fact that they can be formulated free of protein since the conventional mixtures which include an amino acid can be allergenic. As a refattening component, there can be used lauric acid monoglyceride, together with the tenside mixture according to the present invention.

For the solubilization of perfume oils usually employed in such skin cleaning agents, the use of lauryl alcohol ethoxylate has proved to be especially useful since this agent makes oils especially readily soluble.

The shower gel according to the present invention also may include, besides the already-mentioned perfume oil, sodium chloride as a thickening agent and/or the polyfunctional material sodium hexametaphosphate. Furthermore, preserving agents and water can also be present, as well as at least one conditioner, for example a protein hydrolysate and/or an acrylamide polymer.

The shower gels and hair shampoos according to the present invention preferably have a total tenside concentration of below about 10%.

The shower gels and hair shampoos according to the present invention may also include an electrolyte, especially sodium chloride, or a polyphosphte, especially sodium hexametaphosphate, as thickener.

Shower gels according to the present invention preferably have the following amount ratios, expressed in percentages by weight:

| | |
|---|---|
| "Tris" salt of alkyl polyglycol ether carboxylate salt | 2–4.5% |
| sodium lauryl sulphate | 1.5–3.5% |
| fatty acid amidopropylbetaine | 1.5–3% |
| protein hydrolysate | 0.3–1.5% |
| lauryl alcohol ethoxylate | 0.1–0.5% |
| polyquaternium compound (Merquat 550) | 0.2–2% |
| perfume | 0.5–2% |
| sodium hexametaphosphate | 0–5% |
| sodium chloride | 2–10% |
| preserving agent | 0.05–0.5% |
| water | ad 100% |

The following Examples are given for the purpose of illustrating the present invention:

EXAMPLE 1

10% Wash-active substance (WAS) shower gel

| | |
|---|---|
| $C_{12}$-$C_{14}$ ether carboxylic acid, 2.5 mole ethylene oxide, sodium salt | 4.27% |
| sodium lauryl sulphate | 3.25% |
| fatty acid amidopropylbetaine | 2.53% |
| protein hydrolysate | 0.91% |
| glycerol partial esters, ethoxylated | 0.32% |
| perfume oil | 0.72% |
| coloring materials | q.s. |
| Euxyl K 400 | 0.07% |
| sodium chloride | about 2.00% |
| water, sterilized | ad 100% |

(R = coconut or lauryl)
pH value adjusted to 6.5–6.8 with sodium hydroxide or "Tris".

EXAMPLE 2

8% WAS shower gel

| | |
|---|---|
| $C_{12}$-$C_{14}$ ether carboylic acid, 2.5 mole ethylene oxide, sodium salt | 3.39% |
| sodium lauryl sulphate | 2.58% |
| fatty acid amidopropylbetaine | 2.01% |
| protein hydrolysate | 0.72% |
| glycerol partial esters, ethoxylated | 0.26% |
| perfume oil | 0.57% |
| coloring materials | q.s. |
| Euxyl K 400 | 0.07 |
| sodium chloride | about 2.00% |
| water, sterilized | ad 100% |

(R = coconut or lauryl)
pH value adjusted to 6.5–6.8 with sodium hydroxide or "Tris".

EXAMPLE 3

10% WAS hair shampoo

| | |
|---|---|
| $C_{12}$-$C_{14}$ ether carboxylic acid, 2.5 mole ethylene oxide, sodium salt | 4.27% |
| sodium lauryl sulphate | 3.25% |
| fatty acid amidopropylbetaine | 2.53% |
| protein hydrolysate | 0.91% |
| Merquat 550 (hair strengthener) | 1.20% |
| glycerol partial esters, ethoxylated | 0.32% |
| perfume oil | 0.50% |
| coloring materials | q.s. |
| Euxyl K 400 | 0.07% |
| sodium chloride | about 2.00% |
| water, sterilized | ad 100% |

(R = coconut or lauryl)
pH value adjusted to 6.5–6.8 with sodium hydroxide or "Tris".

EXAMPLE 4

8% WAS hair shampoo

| | |
|---|---|
| $C_{12}$-$C_{14}$ ether carboxylic acid, 2.5 mole ethylene oxide, sodium salt | 3.32% |
| sodium lauryl sulphate | 2.58% |
| fatty acid amidopropylbetaine | 2.01% |
| protein hydrolysate | 0.72% |
| Merquat 550 (hair strengthener) | 1.00% |
| glycerol partial esters, ethoxylated | 0.26% |
| perfume oil | 0.57% |
| coloring materials | q.s. |
| Euxyl K 400 | 0.07% |
| sodium chloride | about 2.00% |
| water, sterilized | ad 100% |

(R = coconut or lauryl)
pH value adjusted to 6.5–6.8 with sodium hydroxide or "Tris".

What is claimed is:

1. A shower gel or hair shampoo comprising a neutralized tenside combination of 2–4.5 weight percent alkyl polyglycol ether carboxylate, 1.5–3.5 weight percent alkyl sulphate and 1.5–3 weight percent fatty acid amidopropylbetaine, wherein the alkyl polyglycol ether carboxylate comprises a compound represented by the general formula:

$$R-O-(CH_2-CH_2O)_n-CH_2CO_2^{\ominus} \qquad (I)$$

wherein R is an alkyl radical having up to 20 carbon atoms and n is an integer or fractional number of from 2 to 5, wherein said tenside combination is present in an amount of up to about 10% by weight.

2. A shower gel or hair shampoo as recited in claim 1, wherein R in general formula (I) comprises an alkyl radical having 10 to 16 carbon atoms.

3. A shower gel as recited in claim 2, wherein R in general formula (I) comprises an alkyl radical having 12 to 14 carbon atoms.

4. A shower gel or hair shampoo as recited in claim 1, wherein the alkyl polyglycol ether carboxylate is a mixture of compounds represented by general formula I and n and has an average value of about 2.5.

5. A shower gel or hair shampoo as recited in claim 1, further comprising a neutralizing agent selected from the group consisting of potassium hydroxide, sodium hydroxide and tris-(hydroxymethyl)-aminomethane.

6. A shower gel or hair shampoo as recited in claim 1, wherein the amount ratio of fatty acid amidopropylbetaine to alkyl sulphate to alkyl polyglycol ether carboxylate ranges from about 1:1.5:8 to 1:3.2:4.3.

7. A shower gel or hair shampoo as recited in claim 1, further comprising lauryl alcohol ethoxylate.

8. A shower gel or hair shampoo as recited in claim 1, further comprising at least one conditioner.

9. A shower gel or hair shampoo as recited in claim 8, wherein the conditioner comprises a protein hydrolysate or an acrylamide polymer.

10. A shower gel or hair shampoo as recited in claim 1, further comprising an electrolyte as a thickener present in an amount up to about 10% by weight.

11. A shower gel or hair shampoo as recited in claim 10, wherein the electrolyte comprises sodium chloride.

12. A shower gel or hair shampoo as recited in claim 1, further comprising a polyphosphate as a thickener.

13. A shower gel or hair shampoo as recited in claim 12, wherein the polyphosphate comprises sodium hexametaphosphate.

14. A shower gel or hair shampoo as recited in claim 1, wherein the shower gel or hair shampoo has a pH of about 6.5–6.8.

15. A shower gel or hair shampoo as recited in claim 1, wherein the alkyl polyglycol ether carboxylate is neutralized with an ion selected from the group consisting of sodium, potassium and ammonium.

16. A shower gel or hair shampoo as recited in claim 1, wherein the alkyl polyglycol ether carboxylate is neutralized with tris-(hydroxymethyl)-aminomethane.

17. A shower gel or hair shampoo as recited in claim 10, wherein the shower gel or hair shampoo does not include an additional thickener other than the tenside combination and the electrolyte.

18. A shower gel or hair shampoo comprising, in weight percent:
  about 2–4.5% of a tris-(hydroxymethyl)-aminomethane salt of an alkyl polyglycol ether of carboxylate;
  about 1.5–3.5% of sodium lauryl sulphate;
  about 1.5–3% of fatty acid amidopropylbetaine;
  about 0.3–1.5% of protein hydrolysate;
  about 0.1–0.5% of lauryl alcohol ethoxylate;
  about 0.2–2% of polyquaternium compound;
  about 0.5–2% of perfume;
  about 0–5% of sodium hexametaphosphate;
  about 2–10% of sodium chloride;
  about 0.05–0.5% of preserving agent; and ad 100% water.

* * * * *